United States Patent
Ullrich et al.

(10) Patent No.: US 6,918,923 B2
(45) Date of Patent: *Jul. 19, 2005

(54) RECTANGULAR FRAME ARRANGEMENT WITH ONE TO TWO DISCOID RADIATION FILTERS AND TANNING MODULE

(75) Inventors: Bernd Ullrich, Erlensee (DE); Ulrich Berger, Biebergemünd (DE)

(73) Assignee: Heraeus Noblelight GmbH, Hanau (DE)

( * ) Notice: Subject to any disclaimer, the term of this patent is extended or adjusted under 35 U.S.C. 154(b) by 128 days.

This patent is subject to a terminal disclaimer.

(21) Appl. No.: 10/261,240

(22) Filed: Sep. 30, 2002

(65) Prior Publication Data

US 2003/0078636 A1 Apr. 24, 2003

(30) Foreign Application Priority Data

Oct. 24, 2001 (DE) .......................................... 101 51 841

(51) Int. Cl.[7] ................................................. A61N 5/00
(52) U.S. Cl. ............................. 607/91; 607/88; 607/90; 607/94; 362/362; 362/356; 362/367
(58) Field of Search ............................... 606/9, 10, 13, 606/22; 607/88–91, 93, 94; 362/26, 31, 362–367, 370, 373–375

(56) References Cited

U.S. PATENT DOCUMENTS 5,034,866 A * 7/1991 Pujol .......................... 362/240
5,620,478 A * 4/1997 Eckhouse ..................... 607/88
6,406,509 B1 * 6/2002 Duffy .......................... 55/492
6,806,481 B2 * 10/2004 Ullrich et al. ........... 250/504 R
6,837,900 B2 * 1/2005 Ullrich et al. ................. 607/91

FOREIGN PATENT DOCUMENTS

| DE | 29 41 467 A1 | 4/1981 |
| DE | 36 31 427 C2 | 4/1987 |
| DE | 39 27 695 C2 | 2/1991 |
| DE | 40 37 483 C2 | 5/1992 |
| DE | 195 16 603 A1 | 11/1996 |
| DE | 297 05 097 U1 * | 12/1997 |

* cited by examiner

Primary Examiner—A. Farah
(74) Attorney, Agent, or Firm—Fulbright & Jaworski L.L.P.

(57) ABSTRACT

The invention relates to a rectangular frame arrangement with one to two discoid radiation filters, as well as to a tanning module having such a frame arrangement. The rectangular frame arrangement has four corners and four lateral edges and, on a first lateral edge at least a first spring clip, and on a second lateral edge opposite the first lateral edge at least a second spring clip, the first and the second spring clip being joined together by at least one lateral bar, and at least the first spring clip being U-shaped with a first body portion, a first upper projection and a first bottom projection, a first radiation filter being arranged in a first marginal area between the at least one lateral bar and the first lower projection.

41 Claims, 8 Drawing Sheets

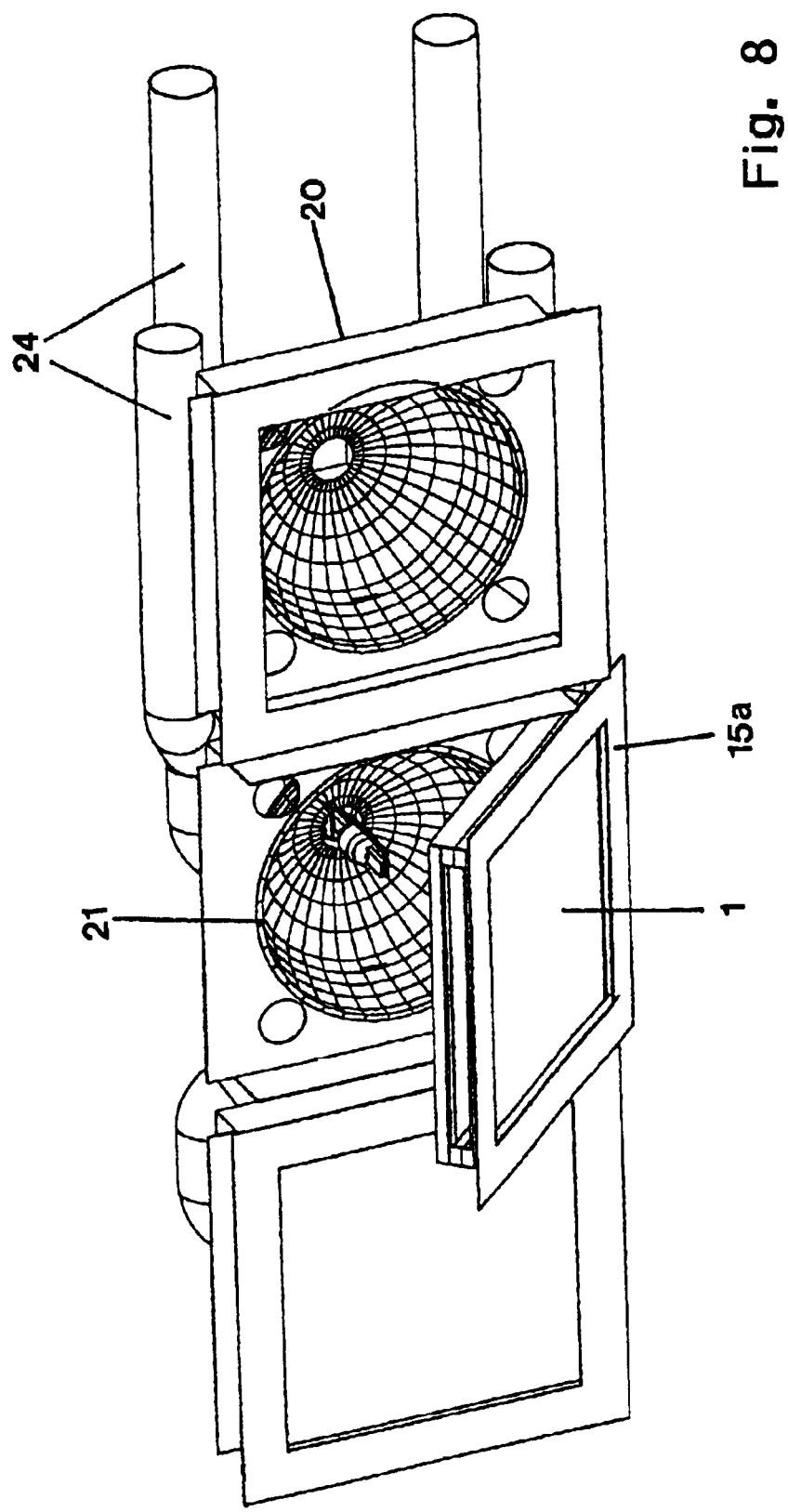

RECTANGULAR FRAME ARRANGEMENT WITH ONE TO TWO DISCOID RADIATION FILTERS AND TANNING MODULE

BACKGROUND AND SUMMARY OF THE INVENTION

The invention relates to a rectangular frame arrangement with one to two discoid radiation filters, as well as to a tanning module having such a frame arrangement. The rectangular frame arrangement has four corners and four lateral edges and, on a first lateral edge at least a first spring clip, and on a second lateral edge opposite the first lateral edge at least a second spring clip, the first and the second spring clip being joined together by at least one lateral bar, and at least the first spring clip being U-shaped with a first body portion, a first upper projection and a first bottom projection, a first radiation filter being arranged in a first marginal area between the at least one lateral bar and the first lower projection.

The invention relates to a rectangular frame arrangement with one to two discoid radiation filters for filtering out a spectrum of a tanning radiator, as well as a tanning module having a frame arrangement of this kind.

The use of discoid radiation filters in tanning apparatus is known. For example, DE 29 41 467 A1 discloses a tanning module with a rectangular housing including a heat filter in one housing wall. In the housing a reflector is arranged wherein an UV filter is situated between the tanning radiator and the heat filter.

DE 195 16 603 A1 discloses a low-pressure viewing field for tanning apparatus, wherein a rectangular housing including reflector and filter plate is used. The housing is suitable for the installation of a plurality of UVC tubes. The side of the filter plate that faces the tubes is coated with a layer of UV phosphor pigments.

DE 36 31 427 G2 describes a radiation apparatus with a rectangular housing a reflector, and a filter plate. To secure the filter plate against breakage a pressure switch is provided which is held by the filter plate in its depressed position, but in case of breakage of the filter plate leaves this position and shuts off the radiation source. The filter plate is fastened in the housing partially by an adhesive layer.

DE 39 27 695 C2 discloses a tanning apparatus with an interference filter disposed for rotation. In the direction of issuance of the radiation, an infrared filter follows the interference filter. According to the inclination of the interference filter in the issuing radiation the limit of the transmission spectrum is shifted to the shorter wavelength UV-B radiation or to the longer wavelength UV-A radiation. Thus the radiation spectrum can be adjusted by turning the filter to the skin type of the person being irradiated.

DE 40 37 483-C2 describes an UV radiation apparatus with prevention against the breakage of a filter glass plate, wherein a current-carrying electrical conductor stripe is disposed on its periphery. If the filter glass plate breaks, the conductor stripe is broken and the current is thereby interrupted and the tanning radiator is shut off.

The problem arises of making available a rectangular frame arrangement with one to two discoid radiation filters so as to permit easy insertion and removal and replacement of the radiation filters. The frame arrangement is to be easy to use in a tanning module.

The problem is solved by a rectangular frame arrangement wherein the frame arrangement has four corners and four lateral edges and has at least a first spring clip on a first lateral edge and on the second lateral edge opposite the first lateral edge at least a second spring clip, the first and second spring clips being joined together by at least one lateral bar and at least the first spring clip is U-shaped, having a first body portion, a first upper projection and a first lower projection, while a first radiation filter is disposed in a first marginal area between the at least one lateral bar and the first lower projection.

Such an arrangement permits a quick and tool-free installation and removal of the radiation filter, since the latter is only clutched by the spring clips but not glued or screwed. The frame arrangement can easily be integrated into a tanning module.

The second spring clip is also preferably U-shaped, with a second body portion an upper projection and a second lower projection.

It is to the advantage of the production of the clamping force if the angle between the clamp body and the first projection as well as between the clamp body and the lower projection is less than 90°. This is true also of the angle between the second clamp body and the upper projection, as well as between the second clamp body and the lower projection.

Of course, the production of clamping force is also possible if the angles between the first clamp body and the first upper lateral projection as well as between the first clamp body and the first lower side projection are equal to 90°, if the first upper and first lower lateral projection have each at least one slot, and if at least one area of the first upper and first lower lateral projection is bent away in the area of the slots with respect to the lateral projection.

Likewise, the angles between the second clamp body and second upper lateral projection and between the second clamp body and the second lower lateral projection can be 90°, in which case the second upper and second clamp body lateral projection having at least one slot, and at least one area of the second upper and second lower lateral projection is bent in the area of the slots toward the particular lateral projection.

Care must be taken, however, to see that a radiation filter must be easy to insert into the spring clip.

For the use of radiation filters of various length it is advantageous if the second clamp body is divided by a step into an upper and lower second clamp body. By means of the step the differences in length of the radiation filter can easily be compensated.

It is advantageous if the upper second clamp body and the lower second clamp body are of different width. Thus the lateral bar can be clasped by the wider second clamp body part to join the first to the second spring clip.

The first radiation filter is preferably arranged in a second marginal area between the at least one lateral bar and the second lower lateral projection.

A second radiation filter is preferably disposed in a first marginal area between the at least one lateral bar and the first upper lateral projection and in a second marginal area between the at least one lateral bar and the second upper lateral projection.

It has proven useful if the spring profiles are formed from spring steel, since spring steel is a low-cost material that is easy to work.

Especially a frame arrangement with two first spring profiles on the first lateral edge and two second profiles on the second lateral edge is preferred, wherein one section joins one of the two first spring clips to one of the two second spring clips, and wherein all four spring clips are arranged each close to one of the four corners of the frame arrangement and the sections are joined to one another by at least one connecting rod.

An especially simple fixation is possible if the first radiation filter has a rectangular circumference. Then the first radiation filter is an interference filter. Preferred is a first radiation filter with a width and a length ranging from 210 mm to 300 mm. Preferably the first radiation filter has a width of 220 mm and a length of 290 mm.

The second radiation filter is ideally an ultraviolet filter or an infrared filter and is preferably rectangular. Preferred is a second radiation filter in a width and length in the range of 210 mm to 290 mm. Especially the second radiation filter has a width of 220 mm and a length of 278 mm.

It has been found practical for the lateral bar to be joined to the body portion of the clip at midpoint between its first upper projection and its first lower projection. It is furthermore advantageous if the lateral bar is joined to the second clip body at midpoint between the second upper projection and the second lower projection.

In case the second spring clip is stepped, the lateral bar is preferably joined to the upper second clip body between the second upper projection and the step. The lateral bar can also, however, be joined to the lower second clip body between the second lower projection and the step.

The upper and/or the lower projections ideally contain an indentation. With such an indentation the projections are angled at their ends remote from the clip body such that the ends at least partially do not lie on the radiation filter but are lifted slightly away from it. This facilitates the insertion of a radiation filter into the spring clips, since a radiation filter is less liable to catch on the indentation than on the end of a projection which is rough in comparison.

To secure the first radiation filter in the frame arrangement, an anti-slip device for the first radiation filter is preferably provided at the lateral edges of the frame arrangement at which no spring clip is present. Likewise advantageous is an anti-slip device for the second radiation filter on the lateral edges of the frame arrangement at which no spring clip is present.

The first radiation filter can have an imprint or an adhesive label on its side facing away from the second radiation filter. In that case it is especially advantageous if the imprint or adhesive label has an opaque marginal area which conceals the holding structure of the radiation filters from the eye of the user.

The problem is furthermore solved by a tanning module with a housing, a three-dimensional reflector disposed in or on the housing, as well as an above-described rectangular frame arrangement on one side of the housing; the first radiation filter covers the radiation exit surface of the reflector, and the upper first projection and the upper second projection of the first spring clip are facing the reflector, while the lower first projection and the lower second projection of the second spring clip are facing away from the reflector.

At the same time the rectangular frame arrangement is preferably releasable from the housing through a swing mechanism and is thus replaceable. The swing mechanism is to permit the radiation filter to be tilted on the housing, and the release of the radiation filter from the housing is to be possible only after the tilted radiation filter has been displaced. Thus a user-friendly exchange of the radiation filter is possible and also the radiation filter is prevented from abruptly dropping down, since by means of such a swing mechanism any dropping of the radiation filter resulting in breakage can be effectively prevented.

The rectangular frame arrangement is ideally hooked into the housing. Especially an opening according to FIG. 7 in the housing is suitable for hooking in the frame arrangement according to the invention.

The rectangular frame arrangement is preferably fixed in position by means of a snap mechanism.

The circumference of the reflector parallel to the radiation exit surface describes preferably a circle, an ellipse, a rectangular or a polygon. It is especially preferred if the reflector is formed of facets and the circumference of the reflector parallel to the radiation exit surface describes a polygon with twelve corners.

It has been found practical if the reflector has a height of 90 mm to 95 mm, especially of 93.6 mm, and the dodecahedron has in the plane of the radiation exit surface a maximum diameter (corner to corner) ranging from 210 mm to 230 mm, especially 210 mm.

It ha furthermore been found practical if the reflector has a height ranging from 110 mm to 125 mm, especially 118.7 mm, and the dodecahedron has in the plane of the radiation exit surface a maximum diameter (corner to corner) ranging from 170 mm to 200 mm, especially 184 mm.

Furthermore, a reflector has been found practical which has a height ranging from 75 mm to 90 mm, especially 83.3 mm, and in which the dodecahedron in the plane of the radiation exit has a maximum diameter (corner to corner) ranging from 205 mm to 235 mm, especially 220 mm.

The drawings in FIGS. 1 to 8 are to explain in an exemplary manner the frame arrangement according to the invention as well as the tanning module.

BRIEF DESCRIPTION OF THE FIGURES

FIG. 8 a three-dimensional drawing of three tanning modules.

DETAILED DESCRIPTION

Figure 1:
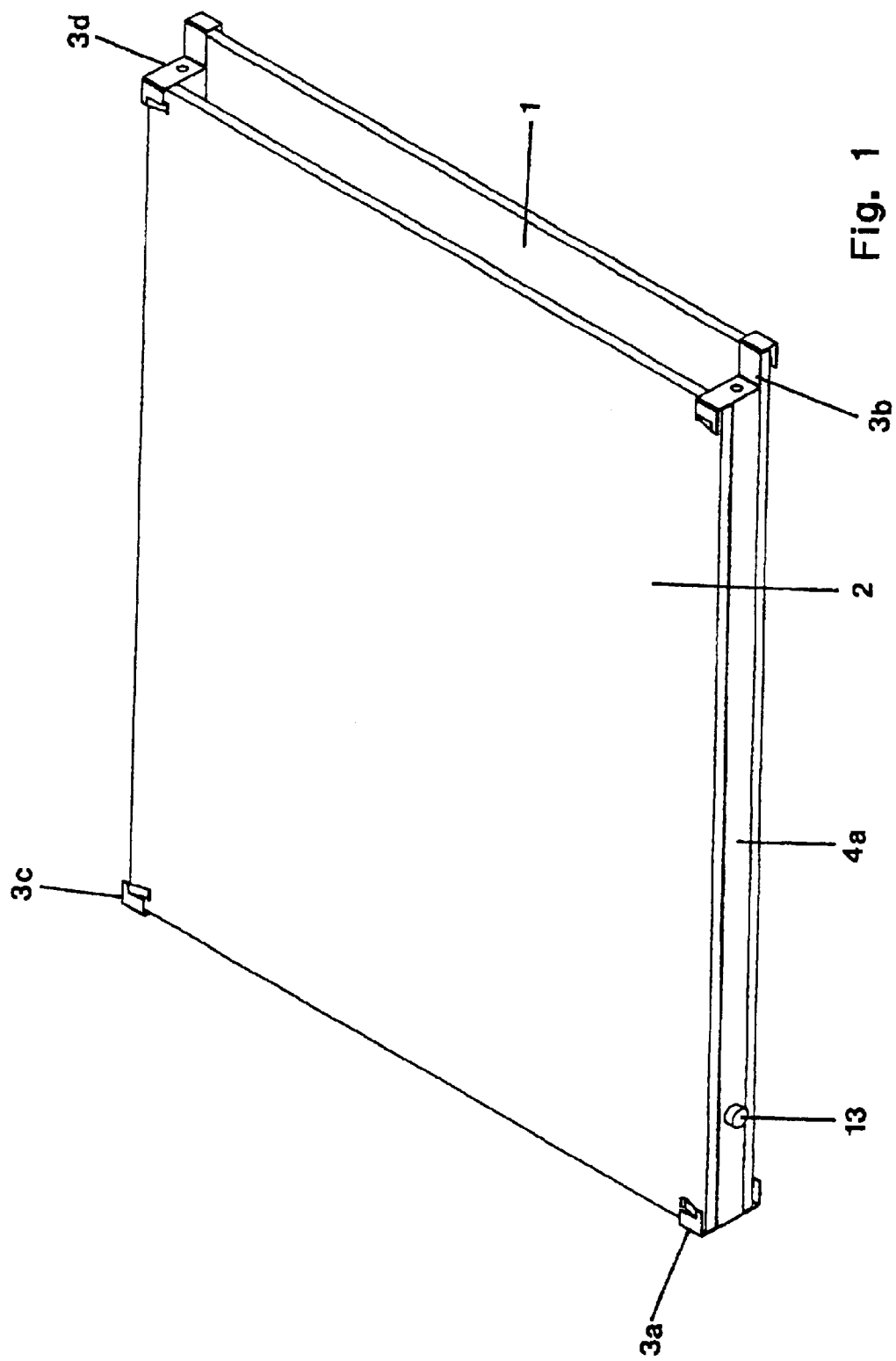
FIG. 1 shows a rectangular frame arrangement in a three-dimensional view.

Thus, FIG. 1 shows a rectangular frame arrangement in a three-dimensional view, in which a first radiation filter 1 and a second radiation filter 2 are present. It is to be added that even only a first radiation filter 1 might be present. Two first spring clips 3*a*, 3*c*, are situated on one lateral edge of the radiation filter and are each connected by lateral bars 4*a* and 4*b* (see also FIG. 2) to a second spring clip 3*b*, 3*d*. The two lateral bars 4*a*, 4*b*, are connected together parallel to one another by a connecting rod 13.

The connecting rod 13 projects on both sides beyond the lateral bars 4*a*, 4*b*, and it is therefore able to hook the frame arrangement into the housing of a tanning module.

Figure 2:
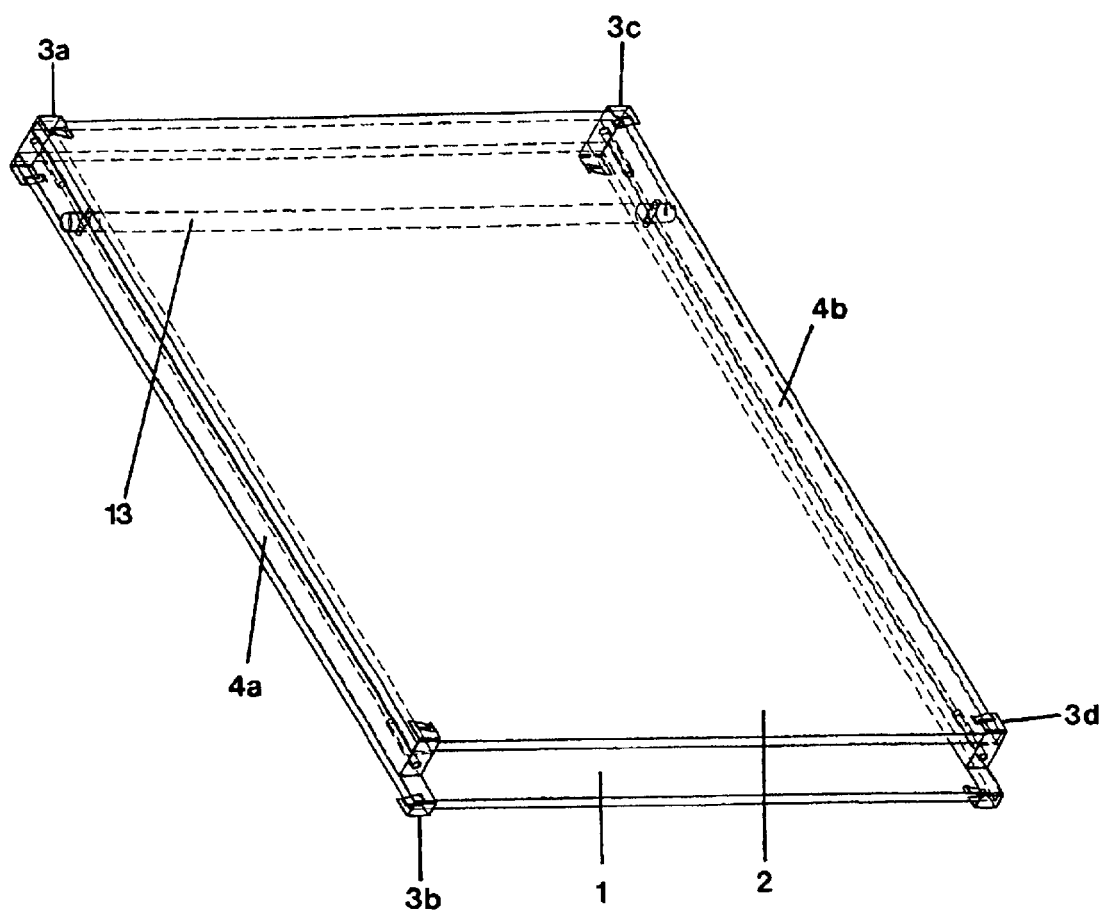
FIG. 2 the frame arrangement of FIG. 1 with all concealed lines.

FIG. 2 shows the frame arrangement from FIG. 1 with all of the hidden lines.

Figure 3A:
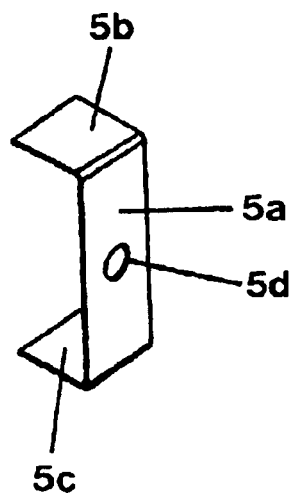
FIG. 3*a* a first spring clip.

FIG. 3a shows a single first spring clip with a first body portion 5a, a first upper projection 5b and a first lower projection 5c. In the first body portion 5a is an opening 5d through which the first spring clip can be attached to a lateral bar 4a, 4b.

Figure 3B:
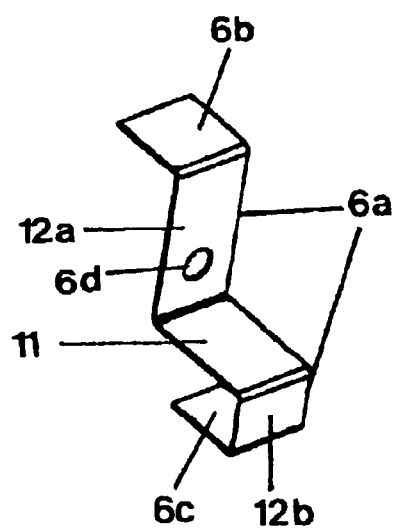
FIG. 3*b* a second spring clip.

FIG. 3b shows a single second spring clip with a second body portion 6a, a second lower projection 6c. In the second body portion 6a is an opening 6d through which the second spring clip can be attached to a lateral bar 4a, 4b. The second body portion 6a is divided by a step 11 into an upper second body portion 12a and a lower second body portion 12b, the opening 6d being situated in the upper second body portion 12a.

Figure 4A:
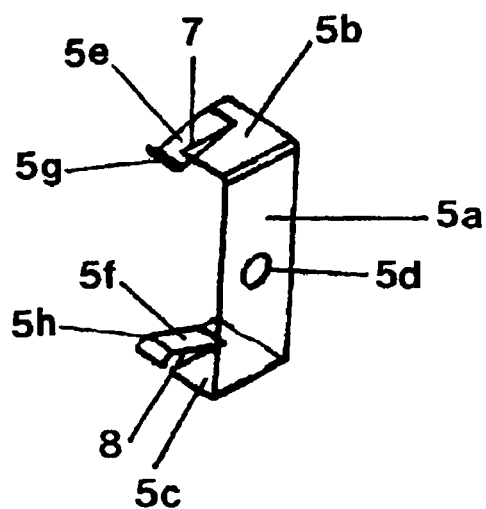
FIG. 4*a* another first spring clip.

FIG. 4a shows another first spring clip which is of more complex shape. It has a first body portion 5a, a first upper projection 5b and a first lower projection 5c. In the first body portion 5a there is an opening 5d through which the first spring clip can be joined to a lateral bar 4a, 4b. The first upper projection 5b has a cut 7 and the first lower projection 5c has a cut 8. In each case at least one area 5e of the first upper projection 5b and an area 5f of the first lower projection 5c is bent toward the opening 5d beginning from the end of the cuts 7 and 8 with regard to the particular projection. In addition, the bent areas 5e, 5f, have each an indentation 5g, 5h. The insertion of a radiation filter into the spring clip is thereby facilitated. In the frame arrangement of FIG. 1 or FIG. 2, the areas 5e, 5f, of the first spring clip 3a, 3c point toward one another. It is, however, just as possible for the areas 5e, 5f, of the first spring clips 3a, 3c, to point away from one another or point in the same direction.

Figure 4B:
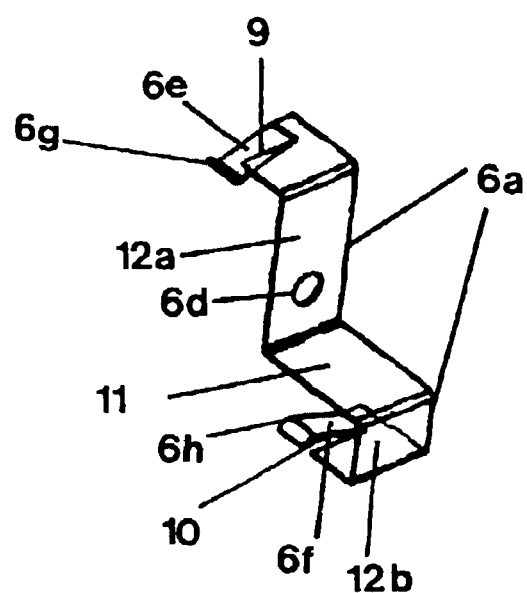
FIG. 4*b* another second spring clip.

FIG. 4b shows another second spring clip which is of more complex shape. It has a second body portion 6a, a second upper projection 6b and a second lower projection 6c. In the second body portion 6a there is an opening 6d through which the second spring clip can be fastened to a lateral bar 6c. The second upper projection 6b has a cut 9 and the second lower projection 6c has a cut 10. In each case at least one area 6e of the second upper projection 6b and an area 6f of the second lower spring clip 6c has a cut 9 running [out] from the end of the cuts 9 and 10 is bent toward the opening 6d. Also, the bent areas 6e, 6f, have each an indentation 6g, 6h. The insertion of a radiation filter into the spring clips is thus facilitated. In the frame arrangement of FIG. 1 or FIG. 2 the areas 6e, 6f, of the first spring clips 3b, 3d, point toward one another. It is, however, just as possible for areas 6e and 6f of the first spring clips 3b, 3d, to point away from one another or point in the same direction.

Figure 5:
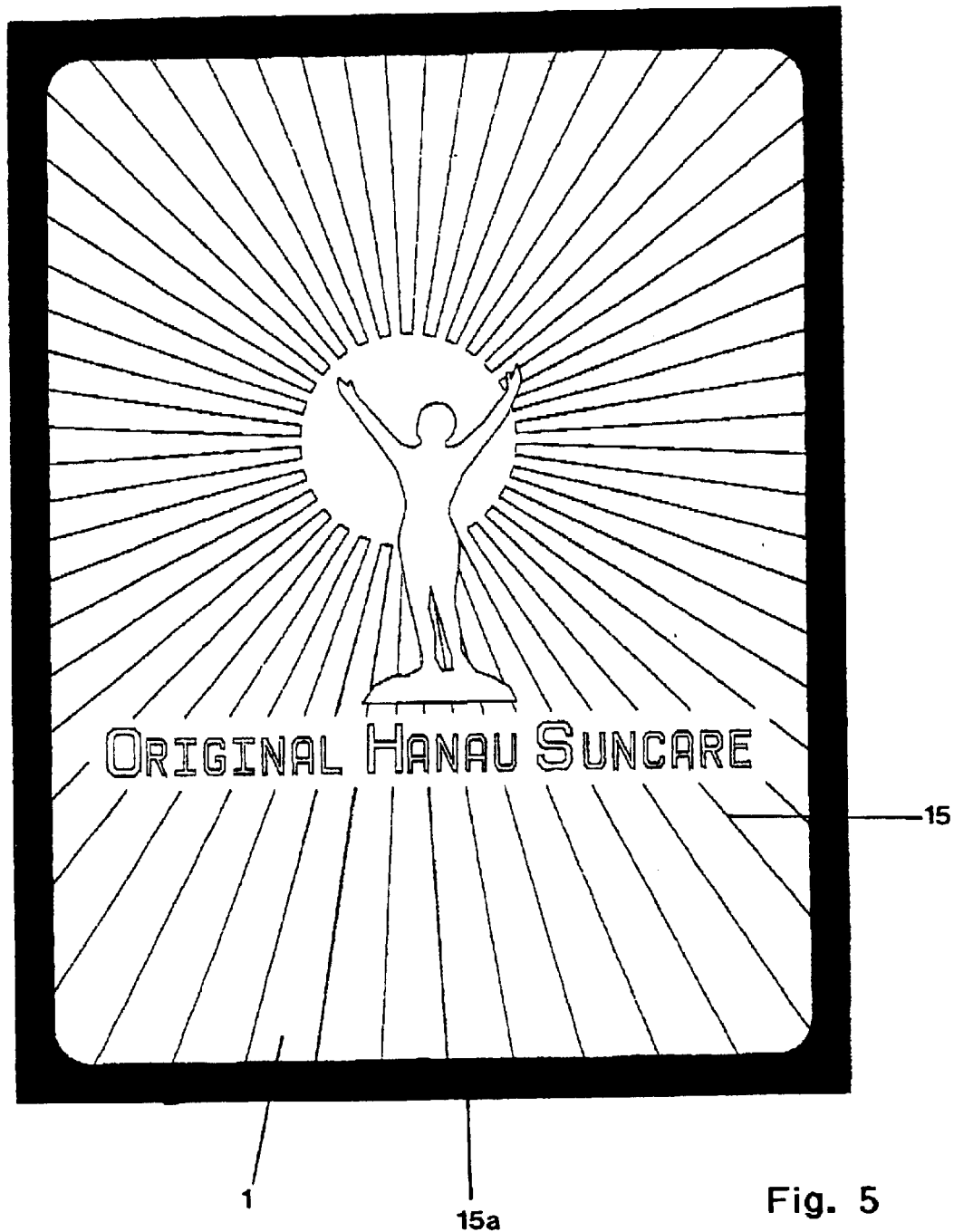
FIG. 5 an image with opaque marginal area.

FIG. 5 shows an imprint 16 with an opaque marginal area 16 on the radiation filter 1 which is intended to mount the radiation filter in front of the eyes of a user.

Figure 6:
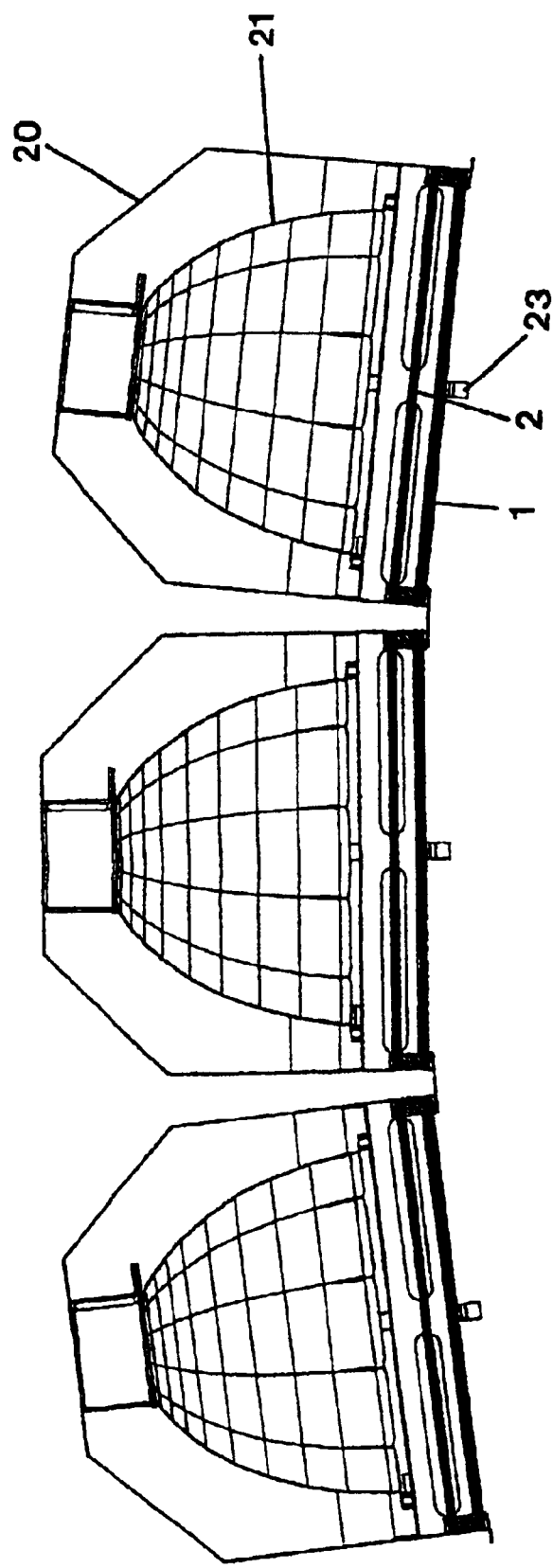
FIG. 6 three tanning modules in section.

FIG. 6 shows in section three tanning modules arranged side by side, each module having a housing 20 and the frame arrangement according to the invention. The reflector 21 can be seen in the housing 20 and the first radiation filter 1 as well as the second radiation filter.

Figure 7:
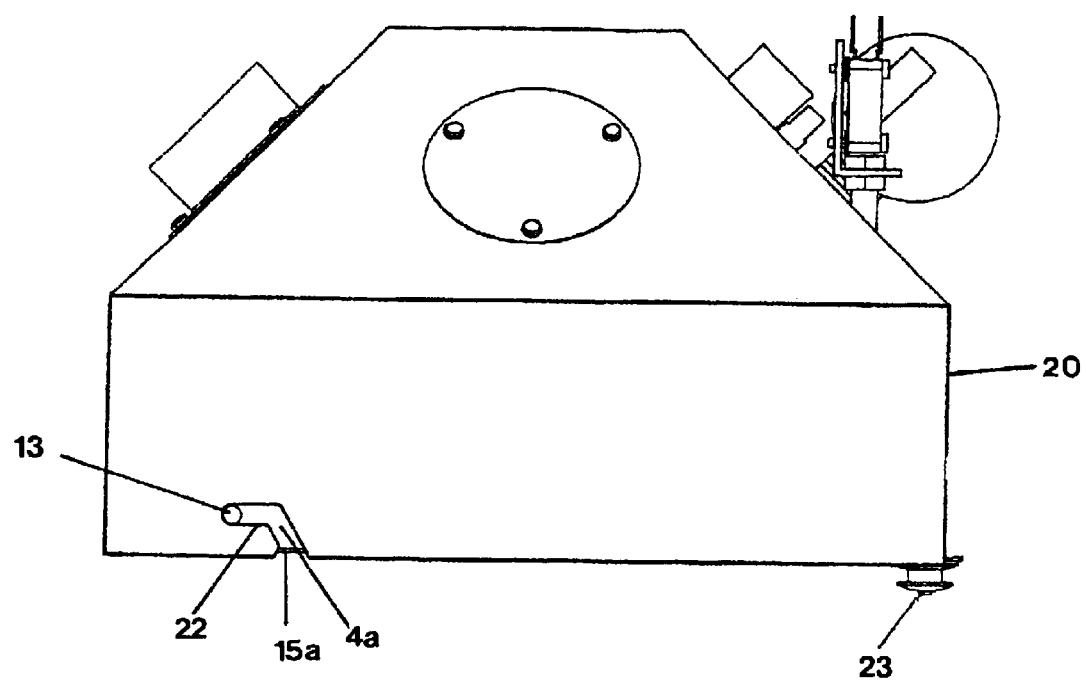
FIG. 7 a three-dimensional drawing of three tanning modules.

FIG. 7 shows how the frame arrangement with the connecting rod 13 is hooked into an opening 22 in the housing 20 through a pivoting mechanism. A lock 23 fixes the frame arrangement in its position (see also FIG. 6).

FIG. 8 is a three-dimensional representation of three tanning modules. On the far left is shown a tanning module with closed frame arrangement. In the middle is shown a tanning module with the frame arrangement folded, including the tanning radiator, wherein the reflector 21, the first radiation filter 1 and the opaque frame 16a can be seen. On the far right is shown a tanning module without radiation filter in the frame arrangement and without tanning radiator. All three tanning modules are provided with air exhaust tubes 24.

It is claimed:

1. A rectangular frame arrangement for use with a tanning radiator comprising:

four corners and four lateral edges;

a first spring clip on a first lateral edge; said first spring clip being U shape and having a first body portion, a first upper projection and a first lower projection;

a second spring clip on a second lateral edge opposite said first lateral edge, at least one lateral bar joining said first spring clip and said second spring clip, wherein a first radiation filter for filtering a spectrum of a tanning radiator is disposed in a first marginal area between said at least one lateral bar and said first lower projection.

2. The rectangular frame arrangement according to claim 1, wherein the angles between said first body portion and said first upper projection and the angles between said first body portion and said first lower projection are less than 90°.

3. The rectangular frame arrangement according to claim 1, wherein the angles between first body portion and first upper projection as well as between first body portion and first lower projection are equal to 90°, that said first upper projection and said first lower projection have at least one cut in each and that at cast one area of said first upper projection and one area of said first lower projection is bent from the end of the cut with regard to the particular projection.

4. The rectangular frame arrangement according to claim 1, wherein the angles between second body portion and second upper projection as well as between second body portion and second lower projection are equal to 90°, in that said second upper projection and said second lower projection have each at least one cut and that at least one area of said second upper projection and one area of said second lower projection is bent starting from the end of the cut with respect to the particular projection.

5. The rectangular frame arrangement according to claim 1, wherein said second spring cup is U-shaped and has second body portion, a second upper projection and a second lower projection.

6. The rectangular frame arrangement according to claim 5, wherein the angles between said first body portion and said first upper projection and the angles between said first body portion and said first lower projection are less than 90°.

7. The rectangular frame arrangement according to claim 5, wherein the angles between said second body portion and said second upper projection and said angles between said second body portion and second lower projection are less than 90°.

8. The rectangular frame arrangement according to claim 5, wherein said first radiation filter is disposed in a second marginal area between said at least one lateral bar and said second lower projection.

9. The rectangular frame arrangement according to claim 5, wherein said second body portion is divided by a step into an upper second body portion and a lower second body portion.

10. The rectangular frame arrangement according to claim 9, wherein said upper second body portion and said lower second body portion are unequally wide.

11. The rectangular frame arrangement according to claim 9, wherein said lateral bar is connected to said upper second body portion.

12. The rectangular frame arrangement according to claim 9, wherein said Lateral bar is connected to said lower second body portion between said second lower projection and said step.

13. The rectangular frame arrangement according to claim 5, wherein a second radiation filter is disposed in a first margin area between said at least one lateral bar and said first upper projection, and in a second marginal area between said at least one lateral bar and said second upper projection.

14. The rectangular frame arrangement according to claim 13, wherein said second radiation filter is an UV filter or an infrared filter.

15. The rectangular frame arrangement according to claim 13, wherein said second radiation filter is rectangular in shape.

16. The rectangular frame arrangement according to claim 1, wherein said first spring clip comprises spring steel.

17. The rectangular frame arrangement according to claim 16, wherein said second spring clip comprises spring steel.

18. The rectangular frame arrangement according to claim 1, wherein two first spring clips are disposed on said first lateral edge and two second spring clips on said second lateral edge, a lateral bar of one of said two first spring clips connecting with one of said two second spring clips, and the total of four spring clips are disposed near one of said four corners of the frame arrangement, and said lateral bars are connected to one another by at least one connecting rod.

19. The rectangular frame arrangement according to claim 18, wherein said first radiation filter is an interference filter.

20. The rectangular frame arrangement according to claim 18, wherein said first radiation filter has a width and a length ranging from 210 mm to 300 mm.

21. The rectangular frame arrangement according to claim 20, wherein said first radiation filter has a width of 220 mm and a length of 290 mm.

22. The rectangular frame arrangement according to claim 21, wherein said second radiation filter has a width and a length ranging from 210 mm to 290 mm.

23. The rectangular frame arrangement according to claim 22, wherein said second radiation filter has a width of 220 mm and a length of 278 mm.

24. The rectangular frame arrangement according to claim 1, wherein said first radiation filter has a rectangular periphery.

25. The rectangular frame arrangement according to claim 1, wherein said lateral bar is connected to said first body portion halfway between said first upper projection and said first lower projection.

26. The rectangular frame arrangement according to claim 1, wherein said lateral bar is connected to said upper second body portion halfway between said second upper projection and said second lower projection.

27. The rectangular frame arrangement according to claim 1, wherein at least one of said upper projections and said lower projections have an indentation.

28. The rectangular frame arrangement according to claim 1, wherein on each of said lateral edges of the frame arrangement at which no spring clip is present, there is disposed a slippage prevention means for said first radiation filter.

29. The rectangular frame arrangement according to claim 1, wherein on each of said lateral edges of the frame arrangement at which no spring clip is present, there is disposed a slippage prevention means for said second radiation filter.

30. The rectangular frame arrangement according to claim 1, wherein said first radiation filter has an imprint or adhesive label on its side facing away from said second radiation filter.

31. The rectangular frame arrangement according to claim 30, wherein said imprint or adhesive label has an opaque marginal area.

32. A tanning module comprising:
   a housing,
   a three-dimensional reflector disposed in or on said housing, and
   a rectangular frame arrangement according to claim 1 on one side of said housing, wherein said first radiation filter covers a radiation exit surface of said reflector, and said upper first projection and said upper second projection of said spring clip face said reflector, said lower first projection and said lower second projection of said spring clip being turned away from said reflector.

33. The tanning module according to claim 32, wherein the rectangular frame arrangement is removable from said housing through a swing mechanism.

34. The tanning module according to claim 33, wherein said rectangular frame arrangement is hooked into said housing.

35. The tanning module according to claim 33, wherein the rectangular frame arrangement is hooked into an opening in said housing.

36. The tanning module according to claim 32, wherein the rectangular frame arrangement is fixed in position by a snap mechanism.

37. The tanning module according to claim 32, wherein said reflector has a height of 90 mm to 95 mm, and said dodecagon in the plane of said radiation exit surface has a maximum diameter as measured corner to corner ranging from 210 mm to 340 mm.

38. The tanning module according to claim 32, wherein a periphery of said reflector parallel to said radiation exit surface describes a circle, an ellipse, a rectangle or a polygon.

39. The tanning module according to claim 38, wherein said reflector is formed of facets and the periphery of said reflector parallel to said radiation exit surface describes a polygon with twelve corners.

40. The tanning module according to claim 39, wherein said reflector has a height ranging from 110 mm to 125 mm, especially of 118.7 mm, and said dodecagon in the plane of said radiation exit surface has a maximum diameter as measured from corner to corner ranging from 170 mm to 200 mm.

41. The tanning module according to claim 39, wherein said reflector has a height ranging from 75 mm to 90 mm, and said dodecagon in the plane of said radiation exit surface has a maximum diameter as measured from corner to corner ranging from 205 mm to 235 mm.

* * * * *